United States Patent [19]

Scholz

[11] Patent Number: 5,206,064

[45] Date of Patent: Apr. 27, 1993

[54] CURABLE RESINS WITH SOLID SUPPORTED ANTIFOAMING AGENTS

[75] Inventor: Matthew T. Scholz, Woodbury, Minn.

[73] Assignee: Minnesota Mining and Manufacturing Company, St. Paul, Minn.

[21] Appl. No.: 687,440

[22] Filed: Apr. 18, 1991

[51] Int. Cl.$^5$ .............. A61L 15/07; A61F 5/04; A61F 13/04; B32B 17/04

[52] U.S. Cl. .............................. 428/86; 428/95; 428/96; 428/240; 428/243; 428/253; 428/255; 428/266; 428/273; 428/321.5; 428/913

[58] Field of Search ............. 428/86, 95, 96, 240, 428/243, 253, 255, 266, 273, 913; 602/8

[56] References Cited

U.S. PATENT DOCUMENTS

| | | | |
|---|---|---|---|
| 3,506,479 | 4/1970 | Breene et al. | 428/96 |
| 3,983,251 | 9/1976 | Singh | 428/329 |
| 4,333,976 | 6/1982 | Okamoto et al. | 428/266 |
| 4,411,262 | 10/1983 | von Bonin | 602/8 |
| 4,502,479 | 3/1985 | Garwood et al. | 602/8 |
| 4,609,578 | 9/1986 | Reed | 428/76 |
| 4,667,661 | 5/1987 | Scholz et al. | 602/8 |
| 4,705,840 | 11/1987 | Buckanin | 528/53 |
| 4,774,937 | 10/1988 | Scholz et al. | 602/8 |
| 4,818,292 | 4/1989 | Iley | 106/210 |

FOREIGN PATENT DOCUMENTS

| | | |
|---|---|---|
| 0206522 | 12/1986 | European Pat. Off. |
| 0223380 | 5/1987 | European Pat. Off. |
| 0266863 | 5/1988 | European Pat. Off. |
| 2220932A | 1/1990 | United Kingdom |

OTHER PUBLICATIONS

International Search Report for corresponding PCT application (3 pages).

ACS Symposium Series 370, "Flavor Encapsulation" Ch. 2, American Chemical Society, Washington, D.C. (1988).

*Primary Examiner*—James C. Cannon
*Attorney, Agent, or Firm*—Gary L. Griswold; Walter N. Kirn; Dale E. Hulse

[57] ABSTRACT

The present invention relates to novel water curable resins and orthopedic casting material incorporating such resins. The water curable resins contain agents which reduce foaming during cure. The agents are formed of an antifoaming composition sorbed on or encapsulated by a solid support. As the resin cures in water, the support disintegrates thereby activating the antifoaming composition. The antifoaming composition is preferably a polysiloxane.

31 Claims, No Drawings

CURABLE RESINS WITH SOLID SUPPORTED ANTIFOAMING AGENTS

BACKGROUND

1. Field of the Invention

The present invention relates to water-curable resins, and in particular, to orthopedic casting materials incorporating such curable resins.

2. The Prior Art

Many different orthopedic casting materials have been developed for use in the immobilization of broken or otherwise injured body parts. One of the first casting materials developed for this purpose was a plaster of Paris bandage.

More recently, water-curable, isocyanate-functional, polyurethane prepolymers were found to be extremely useful in formulating a resin for orthopedic casting materials, as disclosed, for example, in U.S. Pat. No. 4,411,262 (Von Bonin), U.S. Pat. No. 4,502,479 (Garwood et al.), U.S. Pat. No. 4,609,578 (Reed), U.S. Pat. No. 4,667,661 (Scholz et al.), and U.S. Pat. No. 4,774,937 (Scholz et al.). Most commonly, a knitted fiberglass fabric is used as the scrim in combination with the resin.

To initiate the cure of such water curable orthopedic casting materials, the material is contacted with water, typically by immersing a roll of the material in water. Upon immersion, the curing process begins as the isocyanate-functional groups begin polymerizing in the presence of the water. Such polymerization is often aided or controlled by the use of a catalyst, such as is disclosed, for example, in U.S. Pat. No. 4,705,840 (Buckanin). During this curing process, carbon dioxide is formed and released from the resin in the form of bubbles. Unfortunately, the evolution of carbon dioxide bubbles, if not properly controlled, can result in undesirable foaming.

Foaming is undesirable from several standpoints. First, after a roll of orthopedic casting tape has been applied, foaming can cause the end of the tape to percolate up and away from the formed cast. Second, foaming is undesirable because it can decrease layer to layer lamination and hence the strength and durability of the resultant cured orthopedic casting material. Third, foaming can adversely affect the handling characteristics of the material, and can result in undesirable dripping. During cure foaming can occur in the resin (resin phase foaming) or in the aqueous phase (aqueous phase foaming) which is created by the water used to initiate cure. Foaming occurring in the resin phase is the result of carbon dioxide being released through the resin. Resin phase foaming reduces the resin density which weakens the resin and can reduce the overall porosity of the cast through occlusion of the porous scrim. Aqueous (water) phase foaming occurs as the carbon dioxide escaping from the resin bubbles into and through the aqueous phase. Aqueous phase foaming is enhanced due to mechanical manipulation (molding) of the casting tape during application of the tape. Aqueous phase foaming often forms visible sudsing which is esthetically unpleasing and interferes with the handling properties of resin coated casting material.

Commonly assigned U.S. patent application Ser. No. 376,421 filed Jul. 7, 1989, and now abandoned, discloses the use of a stable dispersion of hydrophobic polymeric particles to reduce foaming in the aqueous phase. Such commercially available materials, however, are relatively expensive.

Several antifoaming agents, e.g. DB-100 silicone fluid (Dow Corning) as in U.S. Pat. No. 4,667,661 (Scholz et al.) and silicone Antifoam A (Dow Corning) have been used in the art to suppress foaming in the resin phase.

These latter antifoaming compounds have been effective in retarding foaming occurring within the resin but have not significantly retarded foaming occurring in the aqueous phase during curing. Although not completely understood, it is theorized that such conventional antifoaming compounds tend to remain dispersed, or otherwise entrapped within the polyurethane prepolymer resin. As a result they do not substantially enter into the aqueous phase during curing of the resin to become effective in retarding foaming occurring in that phase during cure.

Solid supported antifoaming materials are known which are composed of an antifoaming compound and a solid support material. Such solid supported antifoaming materials are disclosed for use in agricultural products, detergents, and dry beverages. Solid supported antifoaming compositions disclosed for such uses appear in U.S. Pat. Nos. 3,983,251 and 4,818,292 and in the following patent publications; Great Britain 2,220,932, European Patent publications 0,206,522 and 0,266,863. A commercially available solid supported antifoaming composition (maltodextrin solid support incorporating a polydimethylsiloxane and silica antifoaming composition) is marketed under the trade designation Dow Corning Antifoam 1920 antifoaming agent for bioprocessing.

BRIEF SUMMARY OF THE INVENTION

A principal aspect of the invention is an improved defoaming agent for admixture with water curable resins. The defoaming agents of the invention have particular utility in reducing the amount of aqueous phase foaming during cure of water curable isocyanate-functional polyurethane resins which are impregnated into a fabric sheet material for use in orthopedic casting materials, and other resin impregnated sheets such as pipe wraps and encapsulating materials.

The defoaming agent of the invention has the advantage of reducing the amount of aqueous phase foaming during cure of the isocyanate-functional polyurethane resin without significantly interfering with the tack reduction effect of lubricants which are typically added to the resin to facilitate the moldability and improve the handling characteristics of the cast material during cure.

In another aspect of the invention if the defoaming agent is employed in a mixture with silicone fluid or if the defoaming agent is added in sufficient concentration it reduces the amount of aqueous phase foaming of the polyurethane resin while also enhancing the tack reduction and slipperiness of the resin during cure. The improved antifoaming agent of the invention also retards resin phase foaming. The defoaming agent of the invention when employed in water curable isocyanate-functional resin compositions has the additional property of imparting improved lamination properties and often enhanced strength and durability characteristics of the resin impregnated casting material during and after curing.

The improved defoaming agent of the invention comprises an antifoam composition which is associated with and retained by a solid support. For example, the antifoam composition may be sorbed (e.g., adsorbed or absorbed) onto or encapsulated by the solid support. The solid support is essentially insoluble in the water-curable resin. The solid support, however, has the property that it structurally breaks down (physically or chemically), e.g. disintegrates, in water to allow contact between the water and the antifoam composition. The solid support is typically soluble in water. The solid support may typically be dispersible in water or at least erodible in water. Preferably the solid support is rapidly soluble or rapidly dispersible in water. By soluble is meant the ability to dissolve in water. By dispersible is meant the ability of the solid support to break into small particles which scatter in the water and by erodible is meant the ability of at least a portion of the solid support to break apart in water. The solid support tends to break down in water so that as the water curable resin impregnated fabric sheet contacts water, the solid support in the resin disintegrates allowing antifoaming composition to contact the water. It has been determined that when the solid supported antifoaming agent of the invention is employed, the percent reduction in foaming (e.g. compared to the control formulation Resin A and D) can be typically between about 20% to 90%. Greater concentration of the solid supported antifoam agent up to a point will tend to give a greater reduction in foaming. Various other factors such as water temperature, the amount of water and water immersion time are other factors which can affect the amount reduction of foaming when the solid supported antifoaming agent of the invention is employed. A preferred defoaming agent is comprised of a polysiloxane antifoaming composition which is sorbed (e.g. by adsorption or absorption) onto or encapsulated by a solid support. The solid support is comprised of a material which is a solid at room temperature and may be in the form of a bulk solid, but preferably is in a powder or granular form. The solid support is water soluble or at least water dispersible at room temperature and capable of sorbing or encapsulating the antifoam composition. The solid support is preferably an organic compound which is insoluble in resin but is rapidly soluble, dispersible or erodible in water. Preferred organic supports for the antifoaming composition are sugars, dextrin (hydrolyzed starch), dextran, ethylenediamine stearamide, and polyethoxylated materials. The organic support may include other water soluble polymers and waxes such as modified celluloses, e.g. carboxymethylcellulose, alginates, gelatin, polyethylene oxide/polypropylene oxide copolymers, polyethoxylated fatty alcohols and esters, polyacrylamide, polyvinylalcohol and polyvinylpyrrolidone or combinations thereof. The solid support may also be composed of inorganic oxides, carbonates, sulfates or silicates.

The antifoam composition sorbed onto or encapsulated by the solid support is preferably a polysiloxane of the structure:

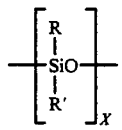

where R and R' are the same or different alkyl groups having from 1 to 6 carbons or aryl groups and X is an integer of at least 20. The alkyl groups containing one to six carbon atoms may be substituted alkyl groups, e.g., acetyl groups. The aryl groups may be substituted aryl groups, e.g., substituted phenyl groups. The preferred antifoam compositions are polydialkylsiloxanes and more preferably polydimethylsiloxanes having molecular weights of between about 500 to 200,000 and viscosities at 25° C. of 100 to 100,000 centipoise, more preferably 1,000 to 30,000 centipoise. These siloxane antifoam compositions may also include hydrophobic silica additives. The polysiloxane compositions typically but not necessarily have trimethylsilyl groups on each end of the polymer chain.

DETAILED DESCRIPTION OF THE PREFERRED EMBODIMENTS

The curable resin materials herein which incorporate the antifoaming agent of the invention exhibit reduced foaming and improved layer to layer lamination. Additionally the antifoaming agent of the present invention when admixed with polydimethylsiloxane having a viscosity preferably of about 100 centistokes, has been discovered to improve tack reduction, i.e., improve slipperiness and handling properties of the resin during cure. These materials have particular utility when used in orthopedic cast applications, however, such is not their only utility. Hence, although the following discussion is set forth in the context of an orthopedic casting material application, it will be appreciated that the applications and uses of the materials of the present invention are not so limited, and a few of the other utilities of the present invention will be noted hereinafter.

The curable resins of the present invention are those resins which employ a water phase during curing where the benefits of the present invention can be realized. Hence, the curable resins of the present invention are water-activated or preferably, water-curable resins. In this regard, water-curable, isocyanate-functional, polyurethane prepolymers are presently preferred.

Preferred resins for use in the present invention include those disclosed in U.S. Pat. No. 4,667,661 (Scholz et al.) and U.S. Pat. No. 4,774,937 (Scholz et al.), which patents are incorporated herein by reference. The polyurethane prepolymer resins disclosed in these patents are formed by the reaction of a polyol with an excess of a polyisocyanate. The resins disclosed in the two aforementioned patents also include tack reducing agents which facilitate application of the orthopedic casting materials. It will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957). Thus, for example, thiols and polyamines could also be used as "polyols" in the present invention, and the term "polyols" will be considered to include such other active hydrogen compounds.

In the present invention the above referenced water curable polyurethane prepolymer resin formulations are modified by adding the solid supported antifoaming composition, described herein, to such formulations. The solid supported antifoaming composition serves to 1) reduce both the amount of aqueous and resin phase foaming during cure 2) increase layer to layer lamination and/or 3) result in cured materials having equivalent or greater strength. It has also been discovered that improved tack reduction and improved handling properties can also be achieved by preparing a premix of the solid supported antifoaming composition and polydimethylsiloxane, preferably having a viscosity of about 100 centistokes. In this case the premix is added to the above referenced water curable prepolymer resin formulations or the polydimethyl siloxane may be separately added to such formulations.

Water curable polyurethane prepolymer resin formulations which included a solid supported antifoaming composition of the invention were prepared. Various comparison tests were made against a control formulation (Resin A) to determine the effectiveness of the antifoaming composition. In addition to foam tests, the layer to layer lamination properties of an orthopedic casting material impregnated with the resin as well as strength and handling properties of such orthopedic casting materials were examined. The various prepolymer resin formulations used in the comparison tests are reported in Table I as Examples A to F. These formulations were prepared in conventional manner wherein the components and each example (Table I) were added, in the order shown to a mixing vessel forming a reaction mixture.

The vessel was equipped with a teflon agitator, nitrogen purge, thermocouple and heating mantle. The reaction mix was maintained in the vessel at a temperature between about 55° C. and 65° C. While this temperature level was maintained, the reaction mix was stirred with the Teflon agitator for a period of about 1 hour after the exothermic reaction or until the isocyanate-polyol reaction was complete denoting formation of the desired polyurethane prepolymer water curable resin. A nitrogen purge was used to maintain the desired dry inert atmosphere. In preparing the polyurethane prepolymer water curable resin by the above described method best results are achieved when the components are maintained dry, added in the order listed and the temperature is controlled as above. Generally when using MEMPE catalyst the polyols are added sequentially or as a mixture in bulk or metered in.

With reference to the prepolymer resin formulation given in Examples A to F (Table I), the "ISONATE" 2143L diisocyanate, available from Dow Chemical Co., is a liquid mixture containing about 73 percent by weight MDI (diphenylmethane diisocyanate) which is a relatively low volatility isocyanate. "NIAX" PPG-425 polyol is a polypropylene oxide liquid diol of (approx.) M.W. 425 "NIAX" PPG-425 formerly available from Union Carbide Corp., is now available from AC West Virginia Polyols Corp. "NIAX" PPG-725 polyol is a polypropylene oxide liquid diol of (approx.) M.W. 750. "NIAX" PPG-725, formerly available from Union Carbide Corp., is now available from A.C. West Virginia Polyols Corp. "PLURONIC" F-108 nonionic surfactant, available from BASF Wyandotte, is a polyethylene oxide-polypropylene oxide block copolymer. It is a solid wax at room temperature and has an approximate molecular weight of 14,500 and a melting point of about 58°-60° C. "PLURONIC" F-108 functions as a lubricant and tack reducing agent which promotes better handling properties of the resin during cure. Benzoyl chloride functions as an acid stabilizer, i.e. it prolongs shelf life presumably by neutralizing residual alkaline materials which may be present in the starting materials. Alkaline materials, if left in the resin prepolymer, can cause premature curing of the resin. MEMPE catalyst is a moisture curing catalyst for curing polyurethane prepolymer resin systems. The MEMPE catalyst as used in the resin formulations herein is 4-[2-[1-methyl-2-(4-morpholinyl)ethoxy]ethyl] morpholine described in commonly assigned U.S. Pat. No. 4,705,840 (Buckanin). Butylated hydroxytoluene (BHT) functions as an antioxidant and thus prevents the occurrence of unwanted ambient oxidation reactions involving any of the components of the formulations. ANTIFOAM 1920 is a water soluble solid supported antifoam composition wherein the support is water soluble or water dispersible (available from Dow Corning Corp). The solid support is disclosed in the product literature as maltodextrin e.g. having the chemical formula $(C_6H_{12}O_5)_n \cdot H_2O$ which is preferably dried to remove water. The molecular weight of maltodextrin in ANTIFOAM 1920 is not disclosed in the product literature. However any water soluble maltodextrin would function adequately. Maltodextrins are discussed in detail in ACS Symposium Series 370, "Flavor Encapsulation," Ch. 2, American Chemical Society, Washington, D.C. The antifoaming composition encapsulated by or sorbed onto the solid support is about 25% by weight polydimethylsiloxane and about 1% by weight amorphous silica Antifoam 1400 compound (formerly DB-100) from Dow Corning Corp., is composed of about 10 wt. % amorphous silica in polydimethylsiloxane. Antifoam 1400 is not a solid supported antifoaming composition. DC-200, silicone at viscosity of 100 centistokes (about 102 centipoise) available from Dow Corning is essentially pure liquid polydimethylsiloxane having a relatively low viscosity of about 100 centistokes.

The water-curable resin can advantageously have the solid supported antifoaming agent of the invention therein in an amount between about 0.1 to 10 percent by weight, preferably between about 0.15 to 5 percent by weight. The water-curable resin can advantageously also include a second antifoaming agent therein, preferably a polydimethylsiloxane (e.g. Antifoam 1400) in an amount between about 0.1 and 5 percent by weight. The second antifoaming agent, if employed, can advantageously be a polydimethylsiloxane having a viscosity at 25° C. of between about 1,000 and 100,000 centipoise. In addition to the solid supported antifoaming agent the water-curable resin can optionally have a relatively low viscosity polydimethylsiloxane therein (e.g. DC-200 silicone). When such a relatively low viscosity polydimethylsiloxane is included it can advantageously have a viscosity between about 50 and 5,000 centipoise at 25° C. In such case the relatively low viscosity polydimethylsiloxane may amount to between about 10 to 75 percent by weight of the total of the low viscosity polydimethylsiloxane and the polydimethylsiloxane in the solid supported antifoaming agent. When added to the water-curable resin, the relatively low viscosity polydimetnylsiloxane functions primarily as a lubricating agent which enhances the tack reduction of the resin during cure.

TABLE I

| Component | Prepolymer Resin A | | Prepolymer Resin B | | Prepolymer Resin C | | Prepolymer Resin D | | Prepolymer Resin E | | Prepolymer Resin F | |
|---|---|---|---|---|---|---|---|---|---|---|---|---|
| | Wt, Grams | Wt. % | Wt, Grams | Wt. % | Wt, Grams | Wt. % | Wt, Grams | Wt. % | Wt, Grams | Wt. % | Wt, Grams | Wt. % |
| Isonate 2143L | 1939.14 | 56.54 | 1939.14 | 56.43 | 1939.14 | 56.43 | 1978.9 | 56.37 | 1978.9 | 56.27 | 2059.5 | 56.58 |

TABLE I-continued

| | | | | | | | | | | | | |
|---|---|---|---|---|---|---|---|---|---|---|---|---|
| Benzoyl Chloride | 1.72 | 0.05 | 1.72 | 0.05 | 1.72 | 0.05 | 1.75 | 0.05 | 1.75 | 0.05 | 1.75 | 0.05 |
| Antifoam 1400 (DB-100) | 6.17 | 0.18 | | | 6.17 | 0.18 | 6.3 | 0.18 | 6.3 | 0.18 | 6.3 | 0.17 |
| BHT | 16.46 | 0.48 | 16.46 | 0.48 | 16.46 | 0.48 | 16.8 | 0.48 | 16.8 | 0.48 | 16.8 | 0.46 |
| MEPE | 45.28 | 1.32 | 45.28 | 1.32 | 45.28 | 1.32 | 46.2 | 1.32 | 46.2 | 1.31 | 46.2 | 1.27 |
| Pluronic F-108 | 141.4 | 4.12 | 141.4 | 4.12 | 141.4 | 4.12 | 144.2 | 4.11 | 144.2 | 4.10 | 140.0 | 3.85 |
| NIAX PPG-425 | 410.04 | 11.95 | 410.04 | 11.93 | 410.04 | 11.93 | 418.25 | 11.91 | 418.25 | 11.89 | 279.9 | 7.69 |
| NIAX PPG-725 | 869.81 | 25.36 | 869.81 | 25.31 | 869.81 | 25.31 | 887.6 | 25.28 | 887.6 | 25.24 | 949.6 | 26.09 |
| BASF Red K3911 HD | | | | | | | 10.5 | 0.30 | 10.5 | 0.30 | | |
| Antifoam 1920 | | | 12.34 | 0.36 | 6.17 | 0.18 | | | 6.17 | 0.18 | | |
| Antifoam 1920 and Silicone Premix[1] | | | | | | | | | | | 140.6 | 3.86 |
| Total | 3430.02 | 100.00 | 3436.19 | 100.00 | 3436.19 | 100.00 | 3510.5 | 100.0 | 3516.7 | 100.0 | 3640.05 | 100.00 |

Notes:
[1]Silicone premix contains 50 wt. % Antifoam 1920 and 50 wt. % DC-200 (100 centistoke viscosity).

Summarized below are tests which were used to determine "foam reduction," "dry strength", "wet strength", and "warm wet strength." Hence, whenever the terms "foam reduction" (or reduced foaming), "dry strength", "wet strength", and "warm wet ring strength" are used, it will be understood that these terms refer to the tests set forth herein below.

Foam Reduction Test

A 12 foot long roll of resin-coated material is taken out of a moisture-proof pouch, equilibrated to 20° C., and immersed completely in deionized water having a temperature of about 80° F. (27° C.) for about 30 seconds. Upon removal the roll is gently sequeezed to remove excess water. In order to observe the foaming of the material during cure, the article is applied around a 2 inch (5.08 centimeter) diameter, 12 inch (30.5 centimeter) section of a mandrel (covered with a thin layer of polyester stockinet such as 3M Synthetic Stockinet MS02) in three overlapping layers. The wrapping around the mandrel is achieved within about 45 seconds from the time the material is removed from the water. After application around the mandrel, the material is aggressively rubbed by hand over its entire length until two minutes has elapsed from the time the pouch is first opened. Visual inspection shows clearly the qualitative degree of foaming, particularly in the water phase, and the approximate duration of the foaming. In this regard, the peak amount of foaming can be estimated in teaspoons.

Delamination Test

This test measured the force necessary to delaminate a cured cylindrical ring of a resin-coated material within the scope of the present invention.

Each cylindrical ring comprised 6 layers of the resin-coated material having an inner diameter of 2 inches (5.08 cm). The width of the ring formed was the same as the width of the resin-coated material employed, namely, 3 inches (7.62 cm). (The final calculation of the delamination strength is given in terms of newtons per centimeter of tape width.) Each cylindrical ring was formed by taking a roll of the resin-coated material from its storage pouch and immersing the roll completely in deionized water having a temperature of about 80° F. (27° C.) for about 30 seconds. The roll of resin-coated material was then removed from the water and the material was wrapped around a 2 inch (5.08 cm) mandrel covered with a thin stockinet (such as 3M Synthetic Stockinet MS02) to form 6 complete uniform layers using a controlled wrapping tension of about 45 grams per centimeter width of the material. A free tail of about 6 inches (15.24 cm) was kept and the balance of the roll was cut off. Each cylinder was completely wound within 30 seconds after its removal from the water.

After 15 to 20 minutes from the initial immersion in water, the cured cylinder was removed from the mandrel, and after 30 minutes from the initial immersion in water its delamination strength was determined.

This was done by placing the free tail of the cylindrical sample in the jaws of the testing machine, namely, an Instron Model 1122 machine, and by placing a spindle through the hollow core of the cylinder so that the cylinder was allowed to rotate freely about the axis of the spindle. The Instron machine was then activated to pull on the free tail of the sample at a speed of about 127 cm/min. the average force required to delaminate the wrapped layers over the first 33 centimeters of the cylinder was then recorded in terms of force per unit width of sample (newtons/cm). For each material, at least 5 samples were tested, and the average delamination force was then calculated and reported as the "delamination strength."

In the practice of the present invention, delamination strengths of up to about 6 pounds/in (14 newtons/cm) have been observed.

Ring Strength Tests

In these tests, the "dry strength", "wet strength", and "warm wet strength", of certain cured cylindrical ring samples of the resin-coated materials of the present invention were determined. For each of these tests, cured cylindrical ring samples were formed as described hereinabove with respect to the delamination test so as to form 6-layered cylinders around a 2-inch (5.08 cm) mandrel, except all excess material was trimmed off to form these cylindrical rings, leaving no tails.

At a point 30 minutes following the initial immersion in water, each cylinder was removed from its respective mandrel and allowed to cure for 48-60 hours in a controlled atmosphere of 75° F.±3° F. (34° C.±2° C.) and 55%±5% relative humidity. Each cylinder was then placed in a fixture in a commercial testing instrument, e.g., an Instron instrument, and compression loads were applied to the cylindrical ring sample along its exterior and parallel to its axis. The cylindrical ring was placed lengthwise between the two bottom bars of the fixture (the bars being 1.9 centimeters wide, 1.3 centimeters in height, and 15.2 centimeters long), with the bars spaced about 4 centimeters apart. The inside edges of the bars were machined to form a curved surface having a ⅛ inch (0.31 cm) radius. A third bar (0.63 cm wide, 2.5 cm high, and 15.2 cm long) was then centered over the top of the cylinder, also parallel to its axis. The bottom or contacting edge of the third bar was machined to form a curved surface having a ⅛ inch (0.31 cm) radius. The third bar was brought down to bear against and crush the cylinder at a speed of about 5 cm/min. The maximum or peak force which was applied while crushing the cylinder was then recorded as the ring strength, which in this particular instance is the "dry strength" (expressed in terms of force per unit length of the cylinder, i.e., newtons/cm). For each material, at least 5 samples were tested, and the average peak force applied was then calculated and reported as the "dry strength".

To measure the "wet strength", the same procedure was followed as for the "dry strength", except that after curing for 48–60 hours, the cylinder was then immersed in water at about 113° F. (45° C.) for about 30 minutes, and then allowed to dry under ambient conditions for about 15 minutes. The cylinder was then placed in the instrument and crushed as described hereinabove in order to determine the "wet strength" thereof.

To determine the "warm wet strength" of the cylinder, the procedure was followed exactly as set forth for the "wet strength" measurement above, with the exception that the cylinder was placed in the fixture and crushed immediately after removal from the 113° F. (45° C.) water bath and was not allowed to dry at all.

When the curable resin of the present invention is intended to be used for orthopedic casting materials, the casting material is prepared by coating the curable resin onto a fabric scrim by standard techniques. Generally, the scrim should be resin loaded to the point where the resin represents from about 35% to about 80% by weight of the total weight of the resin-coated scrim. In the case of a fiberglass scrim, the resin preferably represents from about 35% to about 60% by weight of the total weight of the resin-coated scrim, and preferably from about 38% to about 45% by weight. Manual or mechanical manipulation of the resin (such as by a nip roller or wiper blade) into the scrim is usually not necessary. However, some manipulation of the resin into the fabric may sometimes be desirable to achieve proper impregnation. Care should be given not to stretch the fabric scrim during resin coating, however, so as to preserve the stretchability of the material for its later application around the desired body part.

The curable resins of the present invention may be used with a variety of well-known scrims for use as orthopedic casting materials or for other applications. Although many materials are well-known for this purpose, fiberglass is presently preferred. In this regard, in one presently preferred embodiment of the present invention, the scrim comprises an extensible, heat-set, knitted fiberglass fabric as set forth in U.S. Pat. No. 4,609,578 (Reed), which patent is incorporated herein by reference. One example of a knitted fiberglass scrim which is within the scope of U.S. Pat. No. 4,609,578 is known by 3M, St. Paul, Minn., as the Scotchcast TM 2 knitted fiberglass scrim. The Scotchcast TM 2 scrim is used in the manufacture of 3M's Scotchcast TM 2 and Scotchcast TM Plus orthopedic casting materials.

A series of projections may also be formed along such a knitted fiberglass scrim in order to enhance the lamination properties thereof. A detailed description of scrims having such projections and the enhanced lamination achieved thereby is disclosed in commonly assigned U.S. patent application Ser. No. 376873, filed Jul. 7, 1989 entitled "Orthopedic Casting Materials Having Superior Lamination Characteristics and Methods for Preparing Same"; such patent application is incorporated herein by reference. Such projections can be formed by abrading the scrim with, for example, a knurled roller, a knife edge, sharp or blunt teeth, or by other techniques.

As disclosed in the aforementioned patent application, a projection is considered to be a filament bundle which serves to enhance lamination and typically has 8 or more filaments per bundle. As further set forth in that concurrently filed patent application, the fabric scrims preferably have from about 75 to about 1,500 projections per gram of fabric scrim on the average, more preferably from about 100 to about 1,000 projections per gram of fabric scrim, and most preferably from about 300 to about 700 projections per gram of fabric scrim.

By using the curable resin formulations of the present invention with the improved fabric scrims of the above-mentioned patent application, the benefits of both the improved scrim and the improved resin can be realized in a single resin-coated material, whether used for orthopedic purposes or for other applications.

Orthopedic casting materials prepared in accordance with the present invention are applied to humans or other animals in the same fashion as other known orthopedic casting materials. First, the body member or part to be immobilized is preferably covered with a conventional cast padding and/or stockinet to protect the body part. Next, the curable resin is activated by dipping the orthopedic casting material in water. Excess water may then be squeezed out of the orthopedic casting material, and the material is wrapped or otherwise positioned around the body part so as to properly conform thereto. Preferably, the material is then molded and smoothed to form the best fit possible and to properly secure the body part in the desired position. Although often not necessary, if desired, the orthopedic casting materials may be held in place during cure by wrapping an elastic bandage or other securing means around the curing orthopedic casting material. When curing is complete, the body part is properly immobilized within the orthopedic cast or splint which is formed.

The casting materials formed of curable resins which include the antifoaming agent of the present invention exhibit reduced foaming. The preferred solid supported antifoaming agent of the present invention e.g. Antifoam 1920 (Dow Corning) when admixed with dimethylsiloxane, e.g. DC-200 having a viscosity preferably of about 100 centistokes (about 102 centipoise), or added alone in sufficient concentration (e.g. 5%) has also been discovered to improve tack reduction, i.e. improve slipperiness and handling properties of the casting material during cure.

Foaming can occur in at least two different regions of the orthopedic casting system: the resin phase and the aqueous or water phase. The resin phase is represented by the resin on the scrim which is activated when contacted with water. The water phase is represented by the water which contacts or is otherwise associated with the resin during cure. As the carbon dioxide bubbles are released during cure, they pass both through the resin phase and through the water phase; thus foaming can occur in either or both of these phases. Foaming in the aqueous phase is often clearly visible, as "suds", during cure. Foaming in the resin phase often is not clearly discernible visibly, but it generally causes microscopic voids in the resin which weakens the resin structure. The reduced foaming benefits of the present invention results in easier handling of the casting material during cure.

With reference to Table I resin formulation A is the control. Resin formula B is the same as formula A except that the solid supported antifoaming agent ANTIFOAM 1920 was added and conventional silicone antifoaming agent DB-100 was eliminated. Resin formulation C is the same as the control formulation A except that solid supported ANTIFOAM 1920 was added.

In a first example the prepolymer resin formulations A, B and C (Table I) were coated in a dry environment (relative humidity less than 5%) to a coating weight of 42.5 percent by weight on heat set ECDE 75, 1/0, 0.7 fiberglass knit fabric as described in U.S. Pat. 4,609,578 (Reed) and as used in Scotchcast Plus and "Scotchcast 2" 3 in. casting tape available from 3M. The material was converted into 12 ft. rolls and sealed in aluminum foil composite pouches. These were stored at room temperature for several days and then placed in a refrigerator. Single rolls were removed and allowed to equilibrate at room temperature for 24 hours.

Foam Test

Foam tests on rolls produced from the above resin compositions A, B and C coated on "Scotchcast 2" casting tape were made in accordance with the above described foam reduction test procedure. Rolls produced utilizing resin compositions A, B and C were in turn removed from the pouch, dipped in 23°–25° C. water and squeezed three times under water.

Results

The rolls containing Resins A, B and C were tested after two and four weeks in the refrigerator. Resin foaming appeared to be minimal for all resins indicating that the solid supported antifoaming agent "Antifoam 1920 (Dow Corning) was indeed an effective resin phase antifoam. Aqueous phase foaming, however, was noticeably different among the formulations. At the end of the two week period, Resin A foamed (appeared sudsy and the suds were stable) while Resins B and C did not foam. At the end of four weeks control, Resin A, foamed extensively and the foam was very stable. Resin B had practically no foam and Resin C foamed only slightly.

Rolls containing Resins A, B, and C were also tested by the foam test after they had been stored for 5 months in a refrigerator. Resin A showed the most foaming (about 7-8 teaspoons) with quite a bit of dripping. The drops were cloudy. Resin C showed very little foaming (less than 1 teaspoon) i.e. 86–88% reduction in foam compared to control Resin A and no dripping was observed.

Resin B showed moderate foaming (about 5 teaspoons) i.e. 29–38% reduction in foam compared to control Resin A with a small amount of dripping. The foam was not very stable.

Ring Strength Tests

Physical property strength tests and ring delamination tests were conducted using Resins A, B and C in accordance with the above described procedures. The objective of these tests was to determine if the solid supported antifoaming agent had an effect on dry, wet and warm wet ring strength and ring delamination strength. The results are shown in the following Table II

TABLE II

| Strength Test | Resin A | Resin B | Resin C |
| --- | --- | --- | --- |
| 24 hr Dry (n/cm) | 95.4 | 98.1 | 101.6 |
| 24 hr Wet (n/cm) | Not Measured | 59.5 | 63.0 |
| 24 hr Warm Wet (n/cm) | Not Measured | 26.1 | 26.1 |
| Ring Delamination (n/cm) | 9.5 | 9.3 | 10.0 |

The data demonstrates that the casting tapes containing the preferred antifoam compositions have properties equivalent or superior to the properties of the control casting tape.

In a second example Resins D (control) and E were prepared in accordance with the formulations shown in Table I. The Resins D and E were prepared, coated, converted and tested as in the preceding example. Resin D was prepared by adding 10.5 g of BASF Red K 3911 HD pigment to 3500 g of the formulation shown in control Resin A. Resin E was prepared by adding 6.17 g of Antifoam 1920 to the resin D formulation.

Once again the foam reduction test described in the foregoing was applied. Resins D and E were stored at 4° C. and checked as in the preceding example for resin and aqueous phase foam. The resin phase foaming upon curing was determined to be minimal for both resin D and E. After four weeks in the refrigerator resin D foamed extensively upon curing and the foam drips had a pink hue. Resin E, however, which contained the solid supported ANTIFOAM 1920 had minimal foaming and no color drips upon curing.

In a third example resin F was prepared in accordance with the formulation shown in Table I. Resin F is similar to Resin E except that the solid supported ANTIFOAM 1920 was replaced by a premix prepared by mixing 70 g of ANTIFOAM 1920 (Dow Corning) with an equal amount i.e., 70 g of DC-200 silicone (Dow Corning). (The DC-200 silicone employed was essentially pure liquid polydimethylsiloxane having a relatively low viscosity of about 100 centistokes (about 102 centipoise)).

The resin F was coated, converted, and packaged as described in the first example, except that the actual resin content was 43% by weight. This resin was stored at room temperature and evaluated for its antifoaming and handling properties. Resin F exhibited minimal foaming i.e. of the same degree as Resin E. Additionally, however, Resin F exhibited improved handling characteristics over that of Resin E in that tack reduction (slipperiness) and moldability of the resin coated SCOTCHCAST 2 casting tape appeared to be improved during application and molding. The improved handling characteristics during curing of a Resin F impregnated SCOTCHCAST 2 casting tapes are improved moldability due to a slippery yet creamy feel. The casting tapes made in accordance with the above examples all exhibited desirable set times between about 2 to 18 minutes and for orthopedic applications preferably between 3 to 5 minutes. The set time is the time from initial activation of the material when immersed in water to the time that the material has cured to the point of achieving significant immobilization.

Although the present invention has been described with respect to specific embodiments it should be appreciated that variations of components within any given class is possible without departing from the scope of the invention. The invention, therefore, is not intended to be limited to the specific embodiments but rather is defined by the claims and equivalents thereof.

What is claimed is:

1. An article comprising:
   a fabric sheet; and
   a water-curable resin coated onto said fabric sheet, said resin having an antifoaming agent therein, said antifoaming agent comprising a solid support and an antifoaming composition retained by the solid support, said solid support having the property that it breaks down in water so as to allow contact between the water and the antifoam composition, said antifoaming composition being capable of reducing foaming as said resin cures.

2. An article as in claim 1, wherein said solid support is insoluble in the water-curable resin.

3. An article as in claim 1, wherein the water-curable resin comprises between about 0.1 and 10 percent by weight of the solid supported antifoaming agent.

4. An article as in claim 1, wherein the antifoaming composition is sorbed on the solid support.

5. An article as in claim 1 wherein the antifoaming composition is encapsulated by the solid support.

6. An article as in claim 1 wherein the water-curable resin comprises between about 0.15 and 5 percent by weight of the solid supported antifoaming agent.

7. An article as in claim 1 wherein said water curable resin has a second antifoaming agent therein comprising polydimethylsiloxane having a viscosity between about 1,000 and 100,000 centipoise.

8. An article as in claim 7 wherein the water-curable resin comprises said second antifoaming agent in an amount between about 0.1 to 5 percent by weight.

9. An article as in claim 1, wherein the antifoaming agent reduces foaming in water phase during cure.

10. An article as in claim 9, wherein the antifoaming agent also acts to reduce foaming in resin phase during cure.

11. An article as in claim 1 wherein the solid support is a solid at ambient conditions.

12. An article as in claim 11 wherein the solid support is in granular or powder form.

13. An article as in claim 1 wherein the solid support for the antifoaming agent comprises a material selected from the group consisting of starches, inorganic oxides, carbonates, sulfates, silicates, sugars, dextrin, dextran, waxes, celluloses, alginates, gelatin, polyethylene oxide/polypropylene oxide copolymers, polyethoxylated fatty alcohols, polyethoxylated fatty esters, polyacrylamide, polyvinylalcohol and polyvinylpyrrolidone.

14. An article as in claim 1 wherein the solid support for the antifoaming agent comprises a dextrin.

15. An article according to claim 14 wherein the solid support comprises a maltodextrin.

16. An article as in claim 1 wherein the antifoaming composition comprises a polysiloxane.

17. An article as in claim 16 wherein the polysiloxane is represented by the following formula:

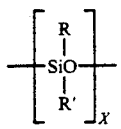

where R and R' are like or different groups selected from the group consisting of alkyl and aryl groups and X is an integer of at least 20.

18. An article as in claim 17 wherein the polysiloxane is a polydimethylsiloxane having a viscosity of between about 100 and 100,000 centipoise at 25° C.

19. An article as in claim 18 wherein the antifoaming composition further comprises amorphous silica.

20. An article as in claim 16 wherein the antifoaming composition comprises a polydimethylsiloxane having a viscosity between about 1,000 and 30,000 centipoise at 25° C. and said water-curable resin comprises another polydimethylsiloxane, said other polydimethylsiloxane having a viscosity of between about 50 and 5,000 centipoise at 25° C. and functioning as a lubricating agent to reduce tack of the resin during cure.

21. An article as in claim 1, wherein said water-curable resin comprises an isocyanate-functional, polyurethane prepolymer.

22. An article as in claim 1, wherein said article is an orthopedic casting material.

23. An orthopedic casting material as in claim 22 wherein said fabric sheet has a plurality of projections on at least one side thereof.

24. An orthopedic casting material as in claim 23 wherein each said projection comprises a bundle of at least about 8 filaments and wherein said side of said fabric sheet has from about 75 to about 1500 projections per gram of fabric sheet.

25. An article as in claim 1 wherein said water-curable resin is an isocyanate functional, polyurethane prepolymer formed by the reaction of a polyol with a polyisocyanate.

26. An article as in claim 1, wherein said fabric sheet comprises fiberglass.

27. An article comprising:
   a fabric sheet; and
   a water-curable resin coated onto said fabric sheet, said resin having an antifoaming agent therein, said antifoaming agent comprising a solid support and an antifoaming composition retained by the solid support, said solid support having the property that it breaks down in water so as to allow contact between the water and the antifoam composition, said antifoaming composition being capable of reducing tack of the resin as said resin cures.

28. A method of applying an orthopedic casting material comprising a fabric sheet and a water-curable resin, said resin having an antifoaming agent therein, said antifoaming agent comprising a solid support and an antifoaming composition being sorbed on or encapsulated by the solid support, said method comprising contacting said casting material with water to initiate curing of said resin, and applying said casting material to a patient, said solid support having the property that it breaks down in water so as to allow contact between the water and the antifoam composition, said antifoaming composition reducing foaming as said resin cures.

29. The method of claim 28 wherein said resin is an isocyanate-functional polyurethane prepolymer.

30. The method of claim 28 wherein said fabric sheet comprises fiberglass.

31. The method of claim 28 wherein during contact of the casting material with water at least about 20% of the solid support disintegrates allowing the antifoaming composition to contact the water, said antifoaming composition having the property of reducing foaming in water phase as said resin cures.

* * * * *

UNITED STATES PATENT AND TRADEMARK OFFICE
CERTIFICATE OF CORRECTION

PATENT NO. : 5,206,064
DATED : April 27, 1993
INVENTOR(S) : Matthew T. Scholz

It is certified that error appears in the above-indentified patent and that said Letters Patent is hereby corrected as shown below:

Col. 1, line 66, please delete ", and now abandoned,".

Signed and Sealed this

Fifth Day of April, 1994

Attest:

BRUCE LEHMAN

Attesting Officer

Commissioner of Patents and Trademarks